United States Patent
Tanaka et al.

(10) Patent No.: US 11,542,647 B2
(45) Date of Patent: Jan. 3, 2023

(54) METHOD FOR MANUFACTURING SHEET FOR USE IN TONGUE PLAQUE CLEANER

(71) Applicants: SHIKIEN CO., LTD., Niigata (JP); NIIGATA UNIVERSITY, Niigata (JP)

(72) Inventors: Michio Tanaka, Niigata (JP); Makoto Inoue, Niigata (JP)

(73) Assignees: SHIKIEN CO., LTD., Niigata (JP); NIIGATA UNIVERSITY, Niigata (JP)

( * ) Notice: Subject to any disclaimer, the term of this patent is extended or adjusted under 35 U.S.C. 154(b) by 191 days.

(21) Appl. No.: 15/897,539

(22) Filed: Feb. 15, 2018

(65) Prior Publication Data
US 2019/0040561 A1 Feb. 7, 2019

(30) Foreign Application Priority Data
Aug. 1, 2017 (JP) .............................. JP2017-149298

(51) Int. Cl.
*D06C 13/08* (2006.01)
*A46D 1/05* (2006.01)
(Continued)

(52) U.S. Cl.
CPC ................ *D06C 13/08* (2013.01); *A46B 9/02* (2013.01); *A46B 9/04* (2013.01); *A46B 15/0081* (2013.01);
(Continued)

(58) Field of Classification Search
CPC ....... A61B 17/244; B29C 59/00; B29C 71/02; B29C 71/0063; B29C 71/0072; B29L 2031/425; D06C 13/08; A46D 1/05
(Continued)

(56) References Cited

U.S. PATENT DOCUMENTS 3,550,223 A * 12/1970 Erb .................... A44B 18/0026
26/9
3,943,592 A * 3/1976 Bhaskar ................. A46B 9/005
15/160
(Continued)

FOREIGN PATENT DOCUMENTS

JP 479390 B 3/1972
JP 57-52408 A 3/1982
(Continued)

OTHER PUBLICATIONS

English Translation of JP-06061107-U; Makino, Tadashi by Schreiber Translation s, Inc. (Year: 1994).*
(Continued)

*Primary Examiner* — Francisco W Tschen
*Assistant Examiner* — Edgaredmanuel Troche
(74) *Attorney, Agent, or Firm* — Leason Ellis LLP; Melvin C. Garner; Mitsuhiro Haraguchi

(57) ABSTRACT

Provided is a method for manufacturing a sheet for use in a tongue plaque cleaner, capable of reliably cutting loops of thread members provided at a given density, and forming thread members each having a shape with an arc portion sufficient enough to scrape off tongue plaque, through steps that are simple, low-cost and suitable for mass production. A method for manufacturing a sheet 1 for use in a tongue plaque cleaner for scraping off tongue plaque, includes: a step of heating a sheet material having multiple looped thread members 2 protruding from one surface of the sheet material, at a temperature below the melting point of the thread members 2; and a step of forming first thread members 3, 8 and second thread members 4, 9 by cutting loops of the thread members 2 heated.

17 Claims, 10 Drawing Sheets

(51) Int. Cl.
- *B26D 1/03* (2006.01)
- *A46B 15/00* (2006.01)
- *A46B 9/04* (2006.01)
- *A46B 9/02* (2006.01)
- *B26D 1/00* (2006.01)
- *B29C 71/02* (2006.01)
- *B26D 1/02* (2006.01)
- *A61B 17/24* (2006.01)
- *B26D 7/10* (2006.01)
- *B29L 31/42* (2006.01)

(52) U.S. Cl.
CPC .............. *A46D 1/05* (2013.01); *A61B 17/244* (2013.01); *B26D 1/0006* (2013.01); *B26D 1/035* (2013.01); *B26D 7/10* (2013.01); *B29C 71/02* (2013.01); *B26D 1/025* (2013.01); *B26D 2001/006* (2013.01); *B29C 2793/009* (2013.01); *B29L 2031/42* (2013.01); *D10B 2509/00* (2013.01)

(58) Field of Classification Search
USPC ........................................................ 264/248
See application file for complete search history.

(56) References Cited

U.S. PATENT DOCUMENTS

| | | | | |
|---|---|---|---|---|
| 4,065,837 A * | 1/1978 | Gierse | ............... | D06C 13/08 26/9 |
| 4,438,541 A * | 3/1984 | Jacob | ............... | A61C 17/00 15/167.1 |
| 4,760,625 A * | 8/1988 | Murasaki | ............ | A44B 18/0026 26/9 |
| 5,379,498 A * | 1/1995 | Nielsen | ............... | D06C 13/08 26/15 R |
| 5,938,673 A * | 8/1999 | DePierro | ............... | A46B 15/00 606/161 |
| 6,248,418 B1 * | 6/2001 | Taguchi | ............... | A41B 3/10 2/171 |
| 6,260,229 B1 * | 7/2001 | Edwards | ............... | A46D 1/00 15/207.2 |
| 6,565,943 B1 | 5/2003 | Kondo et al. | | |
| 6,752,945 B2 * | 6/2004 | Hernandez | ............... | D01F 6/62 264/143 |
| 6,895,624 B2 * | 5/2005 | Fischer | ............... | A61B 17/244 132/308 |
| 8,500,766 B2 * | 8/2013 | Jimenez | ............... | B29C 45/22 606/161 |
| 2003/0044607 A1 * | 3/2003 | Yuuki | ............... | D01F 6/62 428/395 |
| 2007/0255177 A1 * | 11/2007 | Pronovost | ............ | A61B 10/0051 600/573 |
| 2009/0131960 A1 * | 5/2009 | Tanaka | ............... | A61B 17/244 606/161 |
| 2012/0095486 A1 * | 4/2012 | Tanaka | ............... | A46D 3/005 606/161 |
| 2015/0100074 A1 * | 4/2015 | Tanaka | ............... | A46B 15/0081 606/161 |
| 2016/0100850 A1 * | 4/2016 | Tanaka | ............... | A61B 17/244 606/161 |
| 2016/0183959 A1 * | 6/2016 | Tanaka | ............... | A46B 15/0081 264/248 |

FOREIGN PATENT DOCUMENTS

| | | | |
|---|---|---|---|
| JP | 06-61107 U | | 8/1994 |
| JP | 06061107 U | * | 8/1994 |
| JP | 2515465 Y | | 8/1996 |
| JP | 2000-70010 A | | 3/2000 |
| JP | 2002-355121 A | | 12/2002 |
| JP | 2012-095995 A | | 5/2012 |
| JP | 2013-52110 A | | 3/2013 |
| JP | 2013-198672 A | | 10/2013 |
| JP | 2015-073586 A | | 4/2015 |

OTHER PUBLICATIONS

International Search Report dated Oct. 2, 2018 for the corresponding PCT Application No. PCT/JP2018/028719.

Office Action dated Dec. 8, 2020 for the corresponding Japanese Patent Application No. 2019-534542.

Japanese Office Action dated Jun. 3, 2021 for the corresponding Japanese Patent Application No. 2019-534542.

Japanese Office Action dated Sep. 13, 2022 for the corresponding Japanese Patent Application No. 2019-534542 ( 12 pages including English translation ).

* cited by examiner

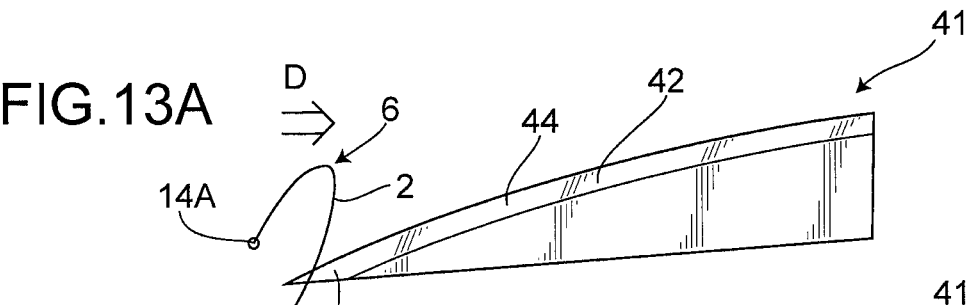
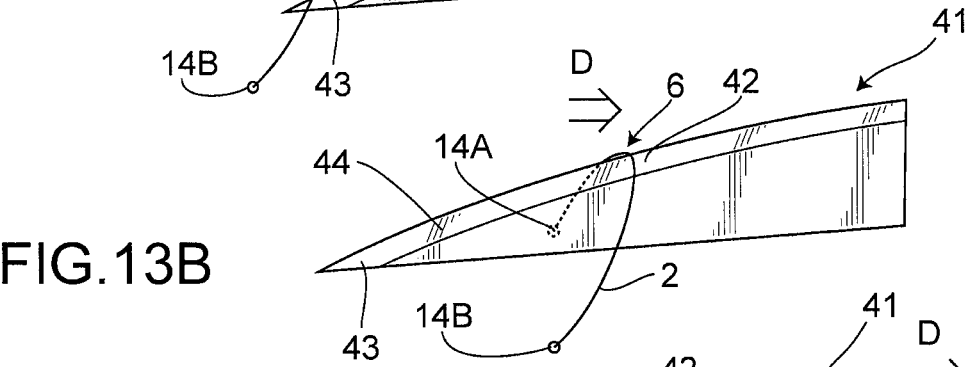
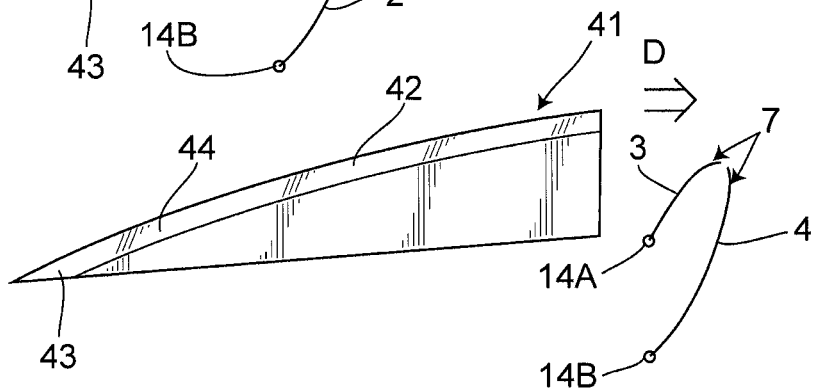
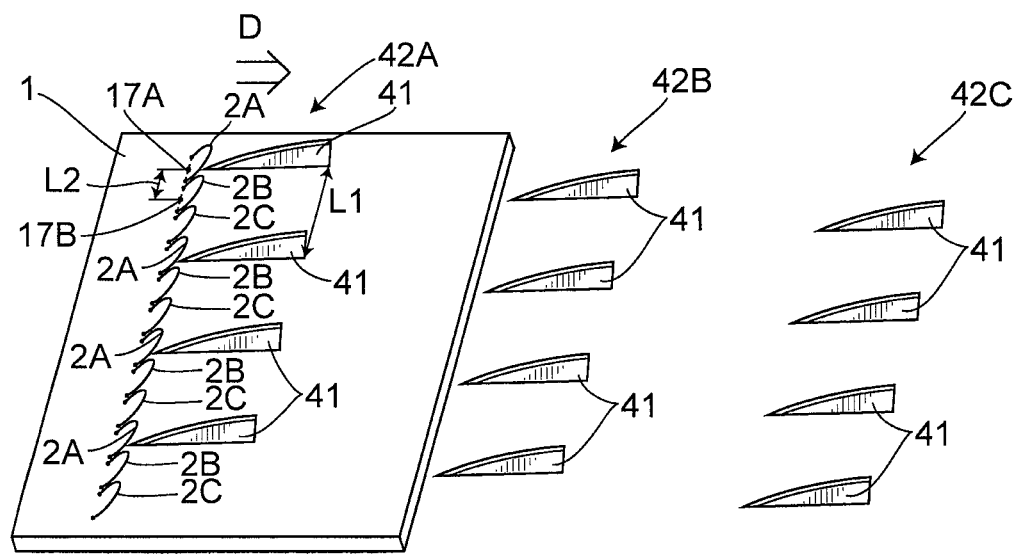
FIG.14

METHOD FOR MANUFACTURING SHEET FOR USE IN TONGUE PLAQUE CLEANER

This application claims the benefit of Japanese Patent Application No. 2017-149298 filed on Aug. 1, 2017, which is incorporated herein in its entirety by reference.

BACKGROUND ART

Field of the Invention

The present invention relates to a method for manufacturing a sheet capable of being used in a tongue plaque cleaner for scraping off tongue plaque.

Background Art

Conventionally, there has been proposed a tongue plaque cleaner having looped thread members on its sheet portion for scraping off tongue plaque when in contact with the tongue (e.g. Japanese registered utility model No. 2515465).

Other than that, there have also been proposed tongue plaque cleaners with thread members each having one end thereof fixed to the sheet portion and the other end thereof serving as a free end, each of such thread members being formed into what can be expressed as the shape of, for example, a hook, a half loop or a reversed J (e.g. JP-A-2013-198672, JP-A-2002-355121 and JP-A-2012-95995).

SUMMARY OF THE INVENTION

As for the sheet of the tongue plaque cleaner in the Japanese registered utility model No. 2515465, the loops of the thread members may, for example, hook on the lingual papillae to damage the tongue, or worse cause bleeding. It is considered that even with the conventional tongue plaque cleaners, the probability for such a kind of incident to happen is not very high. However, it cannot be said that this probability is zero due to the fact that the shapes and sizes of the lingual papillae differ from person to person. Thus, the concern that one's tongue may be damaged cannot be ignored; and since such a type of cleaner is used in the human body, the probability of the aforementioned incident has to be brought closer to zero as much as possible.

As for the sheets of the tongue plaque cleaners in JP-A-2013-198672 and JP-A-2002-355121, since the thread members are formed by hair implantation, it is difficult to increase the number of the thread members per a unit area. For example, in JP-A-2002-355121, the upper limit of the number of the filament units per a unit area in the hair implantation portion is 70 units/cm$^2$.

As for the sheets of the tongue plaque cleaners in JP-A-2013-198672 and JP-A-2012-95995, a method for obtaining hook-like or reversed J-like thread members is such that a cut is made at any site of each looped thread member to cut the same. However, no description is made on a method for resolving the difficulty of forming a cut in each one of the small-diameter loops. Further, simply making a cut will only result in two substantially linear thread members, and may thus fail to turn the thread member(s) into a hook-like or reversed J-like shape with an arc portion sufficient enough to scrape off tongue plaque.

The present invention was made in view of these problems. And, it is an object of the present invention to provide a method for manufacturing a sheet for use in a tongue plaque cleaner, capable of reliably cutting loops of thread members provided at a given density, and forming thread members each having a shape with an arc portion sufficient enough to scrape off tongue plaque, through steps that are simple, low-cost and suitable for mass production.

A tongue plaque cleaner sheet manufacturing method according to one of the features of the present invention for solving the above problems, includes a step of heating a sheet material having multiple looped thread members protruding from one surface of the sheet material, at a temperature below the melting point of the thread members; and a step of forming first and second thread members by cutting one part of each of the loops of the thread members heated.

According to the tongue plaque cleaner sheet manufacturing method of the invention, there can be manufactured a sheet capable of efficiently removing tongue plaque without damaging the tongue, through simple and low-cost steps.

BRIEF DESCRIPTION OF THE DRAWINGS

FIG. 3A to FIG. 3C are diagrams showing how grime (tongue plaque) adhering to the lingual papillae is scraped off by a thread member(s) formed according to a first embodiment of the invention, in which FIG. 3A shows how the thread member comes into contact with a lingual papilla; FIG. 3B shows how the thread member scrapes through the lingual papilla; and FIG. 3C shows a state where the thread member has already scraped through the lingual papilla.

FIG. 9A and FIG. 9B are diagrams showing how a state of a thread member changes when a top-vicinity region of the loop of the thread member is cut without performing a heating treatment thereon in advance, in which FIG. 9A shows a thread member prior to cutting; and FIG. 9B shows a thread member that has been cut.

FIG. 10A and FIG. 10B are diagrams showing how a state of a thread member changes when a top-vicinity region of the loop of the heat-treated thread member is cut, in which FIG. 10A shows a thread member prior to cutting; and FIG. 10B shows a thread member that has been cut.

FIG. 13A to FIG. 13C are perspective views showing a method for cutting the top-vicinity region of the loop of each thread member, according to the first embodiment of the invention, in which FIG. 13A shows how a thread member moves toward a cutting device; FIG. 13B shows how the thread member comes into contact with a cutting portion of the cutting device; and FIG. 13C shows a state where the thread member has been cut by the cutting device.

FIG. 14 is a perspective view showing a method for cutting the thread members of the first embodiment of the invention.

FIG. 18A to FIG. 18D are diagrams showing how grime (tongue plaque) adhering to lingual papillae is scraped off by the thread members formed according to the second embodiment of the invention, in which FIG. 18A shows how the thread member comes into contact with a lingual papilla; FIG. 18B shows how the thread member is deformed along the lingual papilla; FIG. 18C shows how the thread member scrapes through the lingual papilla; and FIG. 18D shows a state where the thread member has already scraped through the lingual papilla.

FIG. 19A to FIG. 19C are perspective views showing a method for cutting a side part of the thread member, according to a second embodiment of the invention, in which FIG. 19A shows how the thread member moves toward a cutting device; FIG. 19B shows how the thread member comes into contact with a cutting portion of the cutting device; and FIG. 19C shows a state where the thread member has been cut by the cutting device.

DETAILED DESCRIPTION OF THE INVENTION

Embodiments of the present invention are described hereunder with reference to the accompanying drawings. However, the embodiments described below shall not limit the contents of the invention that are described in the claims. Further, not all the elements shown hereunder are necessarily the essential elements of the invention.

Tongue Plaque Cleaner

Figure 1:
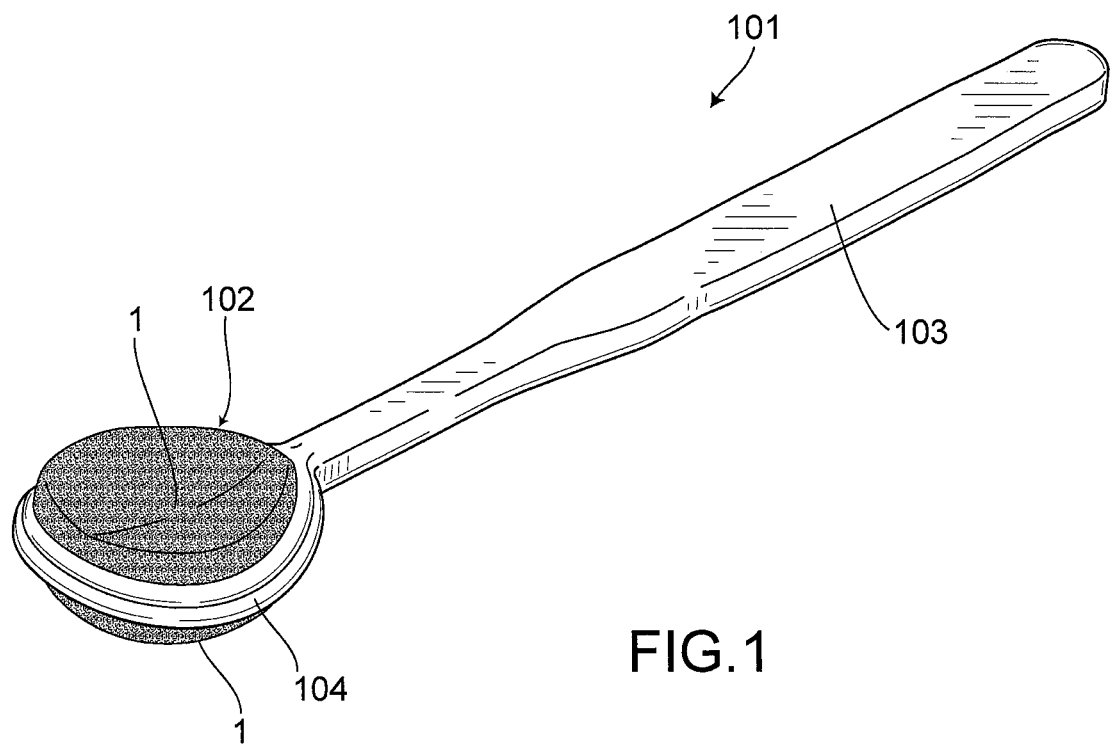
FIG. 1 is a perspective view showing an example of a tongue plaque cleaner using a tongue plaque cleaner sheet of an embodiment(s) of the present invention.

FIG. 1 shows an example of a tongue plaque cleaner 101 using a sheet for tongue plaque cleaner 1 (also referred to as "sheet" hereunder) that is manufactured in accordance with an embodiment of the invention. This tongue plaque cleaner 101 has a head portion 102 formed into a thin and flattened shape. The sheet 1 having a thread material on its surface is provided on both surfaces of the head portion 102. This sheet 1 is fixed to the side surface of the head portion 102 through a ring portion 104 integrally formed with a rod-shaped gripper. A user can hold the rod-shaped gripper 103, and press the sheet 1 against his or her tongue so as to move the cleaner 101 back and forth.

Figure 2:
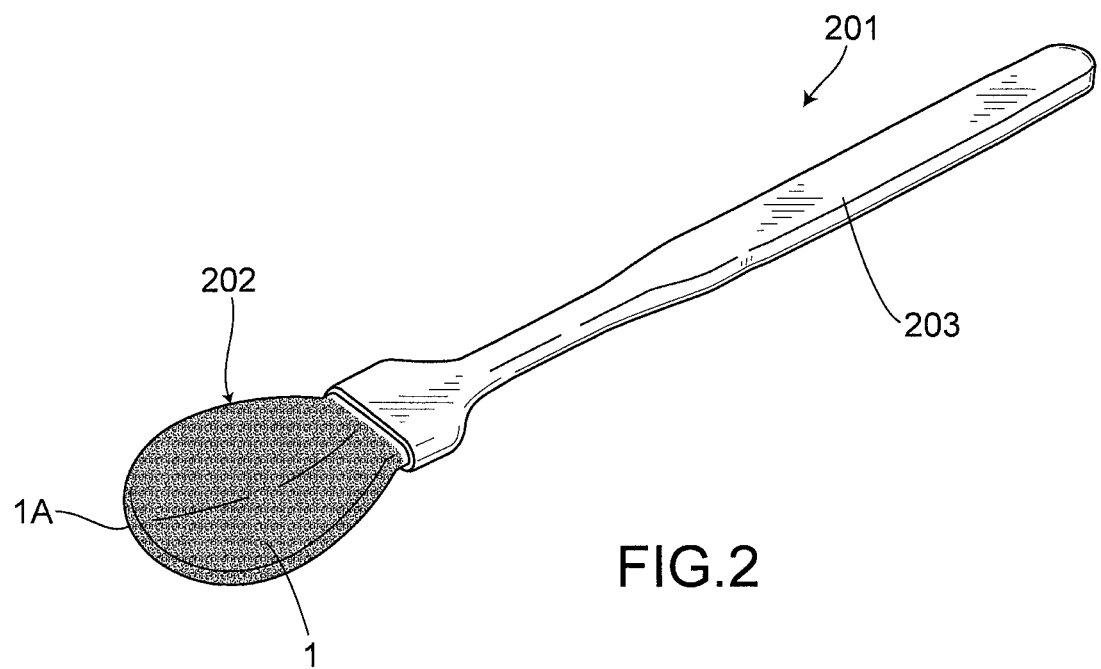
FIG. 2 is a perspective view showing another example of the tongue plaque cleaner using the tongue plaque cleaner sheet of the embodiment of the present invention, this example being different from the example shown in FIG. 1.

FIG. 2 shows another example of a tongue plaque cleaner 201 using the sheet for tongue plaque cleaner 1 that is manufactured in accordance with the embodiment of the invention. The tongue plaque cleaner 201 differs from the tongue plaque cleaner 101 shown in FIG. 1 in that the sheet 1 is formed into the shape of a pouch with the thread material being present on the outer surface thereof, and that a head portion 202 substantially linearly arranged with a rod-shaped gripper 203 is covered by such pouch-shaped sheet 1. That is, the tongue plaque cleaner shown in FIG. 2 does not have the ring portion 104 shown in FIG. 1, but has the thread material arranged on the entire outer surface of the head portion 202.

Described hereunder are embodiments of a method for manufacturing the sheet for tongue plaque cleaner 1 of the present invention.

First Embodiment

Structure of Sheet

Figures 3A, 3B, 3C:
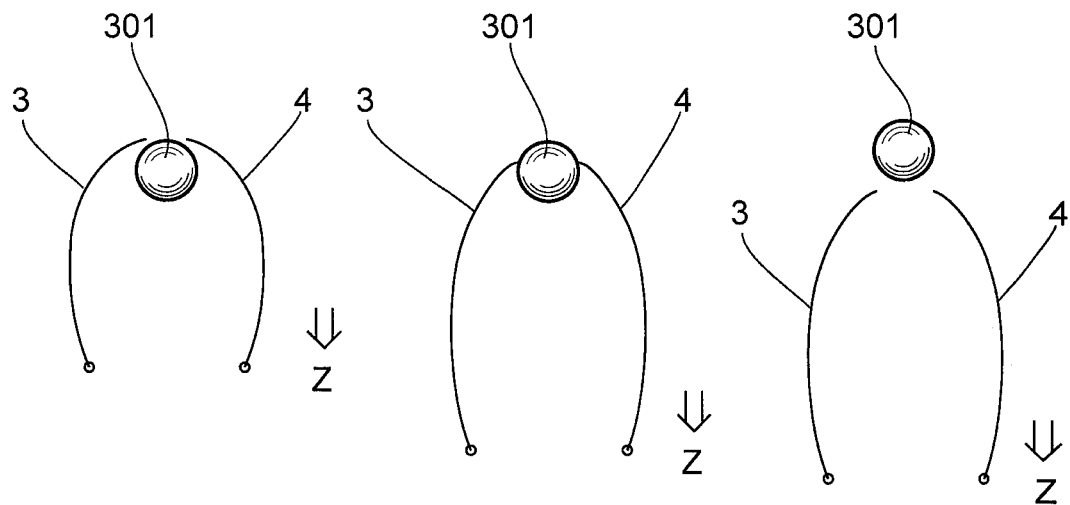

Numerous fine mucosal projections called lingual papillae 301 as shown in FIG. 3A exist on, for example, the surface and side surface of a tongue. Such lingual papillae 301 have a size of, for example, about 0.5 to 1 mm each, though it may vary from person to person. In order to scrape off a grime (tongue plaque) adhering to these fine lingual papillae 301, there may be used, for example, a loop pile having small loop-shaped thread members 302.

Figure 7:
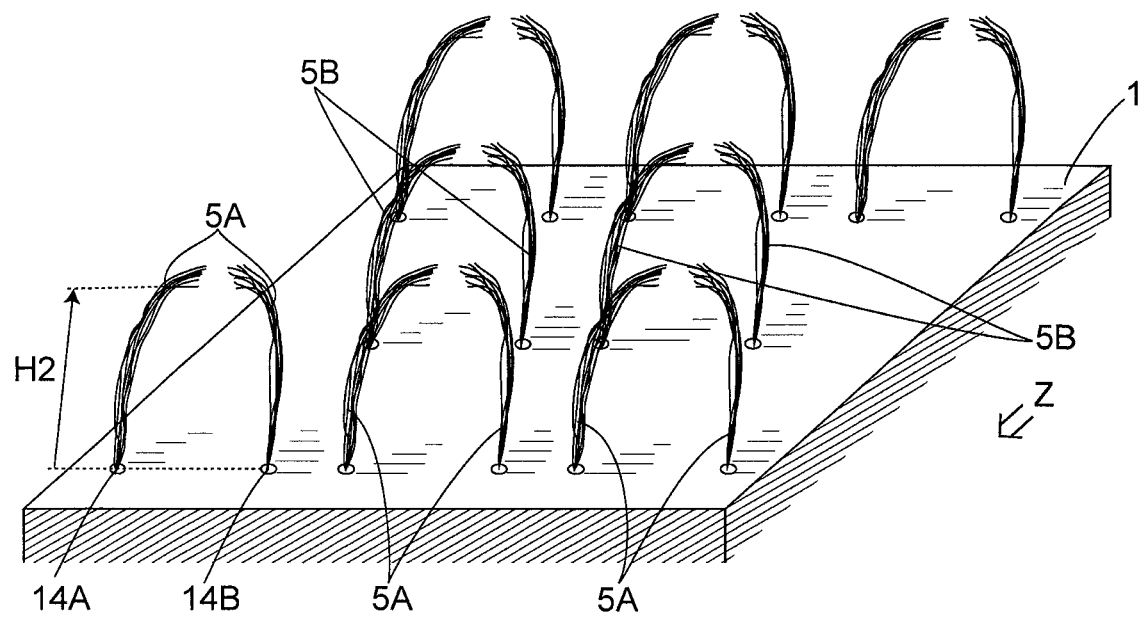
FIG. 7 is a perspective view of a sheet having the thread members formed according to the first embodiment of the invention.
Figure 12:
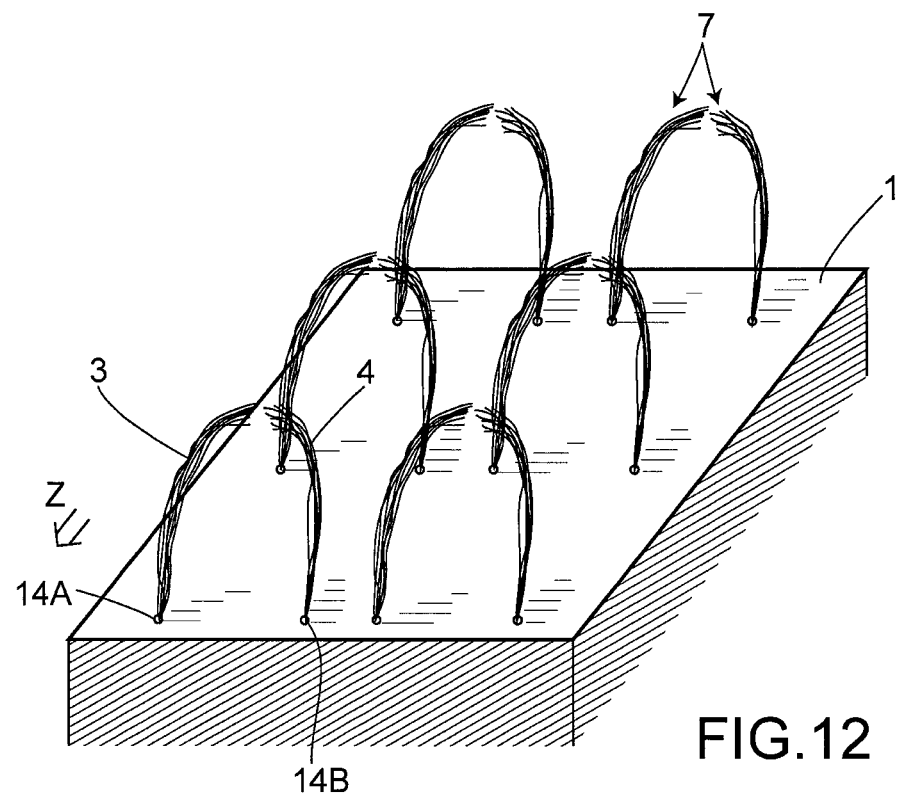
FIG. 12 is a perspective view showing a sheet having the thread members formed according to the first embodiment of the invention.

In this regard, FIGS. 3A to 3C show how the grime adhering to the lingual papillae 301 is scraped off by a first thread member 3 and a second thread member 4 that are formed by cutting a part of a loop in accordance with a manufacturing method of the present embodiment. When moved in a moving direction Z, the first and second thread members 3, 4 will move along the lingual papillae 301, and scrape therethrough in a manner such that the grime adhering to the circumferences of the lingual papillae 301 will be scraped off. Therefore, the sheet 1 having the first and second thread members 3, 4 as shown in FIG. 7 and FIG. 12 is capable of cleanly removing tongue plaque without damaging the lingual papillae 301.

It is preferred that a pile-woven sheet such as a pile fabric be employed as the sheet 1. However, there may also be employed a woven sheet such as twill woven sheet and a sateen woven sheet; or a non-woven sheet. Examples of a material of the sheet include polyamide fibers such as nylon (registered trademark); polyester fibers such as polyethylene terephthalate and polybutylene terephthalate; and polyolefin-based fibers such as polyethylene and polypropylene. Among these materials, preferred are polyamide fibers such as nylon (registered trademark) as one of thermal plastic resins. Other than the materials mentioned above, there may also be employed an animal hair such as horse hair and swine hair, as the thread material.

Figure 4:
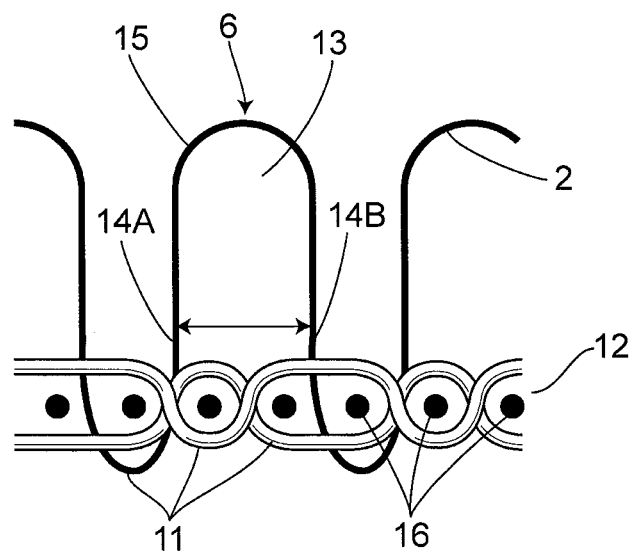
FIG. 4 is a cross-sectional view of a pile fabric having unprocessed thread members of a loop pile.

FIG. 4 is a cross-sectional view of an unprocessed pile fabric. In the case of a pile-woven fabric, the pile-woven fabric is woven in a way such that a part of its warps (pile yarns 11, foundation warps) are sticking out of the surface of a pile-woven foundation main body 12, as thread members 2 each made of a loop-shaped ring 13. Each thread member 302 has a pair of a first protruding portion 14A and a second protruding portion 14B that are raised; and a bridge portion 15 bridging over a gap between the tips of the first protruding portion 14A and the second protruding portion 14B, and being formed into a shape with a substantially central part thereof bulging upward in an arc-like fashion. A numerical symbol "16" denotes wefts. A direction along a width W between the first protruding portion 14A and the second protruding portion 14B intersects with a moving direction Z, and is preferably orthogonal thereto.

Figure 5:
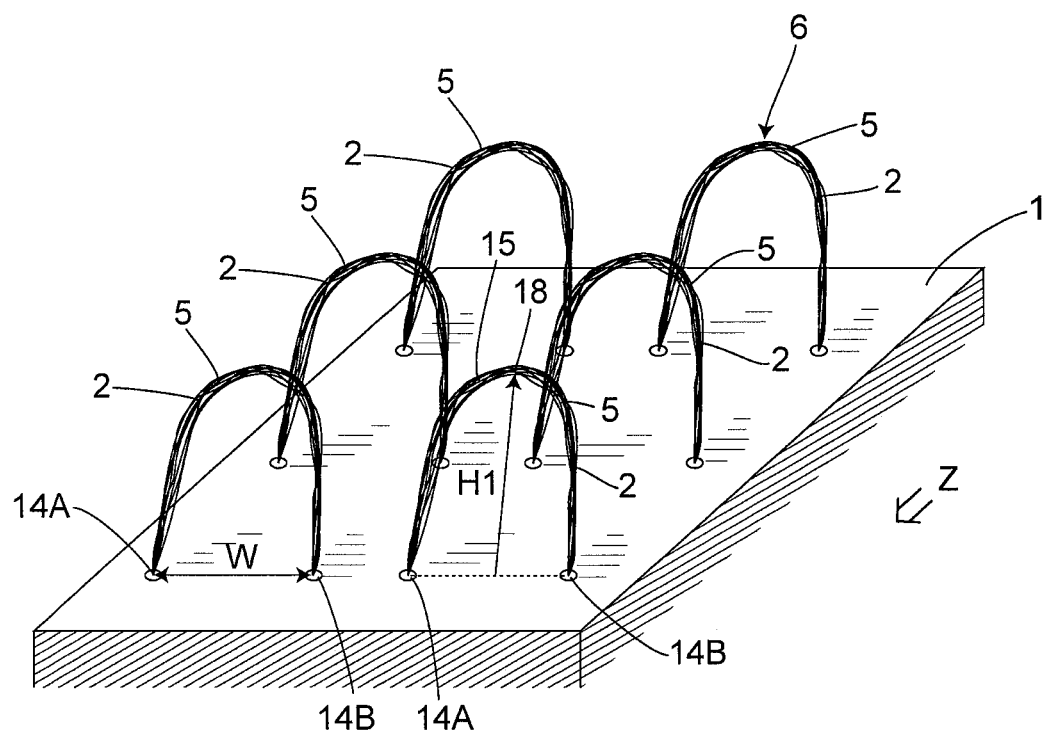
FIG. 5 is a perspective view of a sheet having unprocessed thread members of a loop pile.

As shown in FIG. 5, bundles of multiple thread members 2, approximately 10 in each bundle, are provided on one surface of the unprocessed sheet 1 in a manner such that the thread members 2 in each bundle rise from an identical pair of the first and second protruding portions 14A, 14B. The shapes of the thread members 2 rising from an identical pair of the first and second protruding portions 14A, 14B are substantially identical to one another. When a group of the thread members 2 rising from an identical pair of the first and second protruding portions 14 is defined as a thread member group 5, and the shape of the thread member 2 in one thread member group 5 is compared to those of other thread member groups 5, even the shapes of the thread members 2 in each thread member group 5 are substantially identical to one another.

There are no particular restrictions on the thickness of each thread member 2 and the number of the loops. They may be determined in consideration of materials or the like. For example, when using nylon (registered trademark) as the material for the thread members 2, it is preferred that the thickness of each thread member 2 be, for example, about 200 to 400 denier, and that the number of the loops be, for example, about 1,500 to 2,500 per 1 cm squared. This configuration allows the user to efficiently scrape off tongue plaque with a soft contact feeling.

Although there are no particular restrictions on a height from the tips of the first and second protruding portions 14A, 14B to a top point 17 of the bridge portion 15 i.e. a loop height H1 of the thread member 2, it is preferred that such height be, for example, about 1 to 5 mm. It is preferred that a height H2 of each of the cut first and second thread members 3, 4 also be about the same height as the height H1. If the heights are excessively low, tongue plaque may not be scraped off sufficiently. If the heights are excessively high, the thread members may bow easily such that forces may not be transmitted in a sufficient manner, which leads to a concern that tongue plaque cannot be scraped off efficiently.

Figure 6:
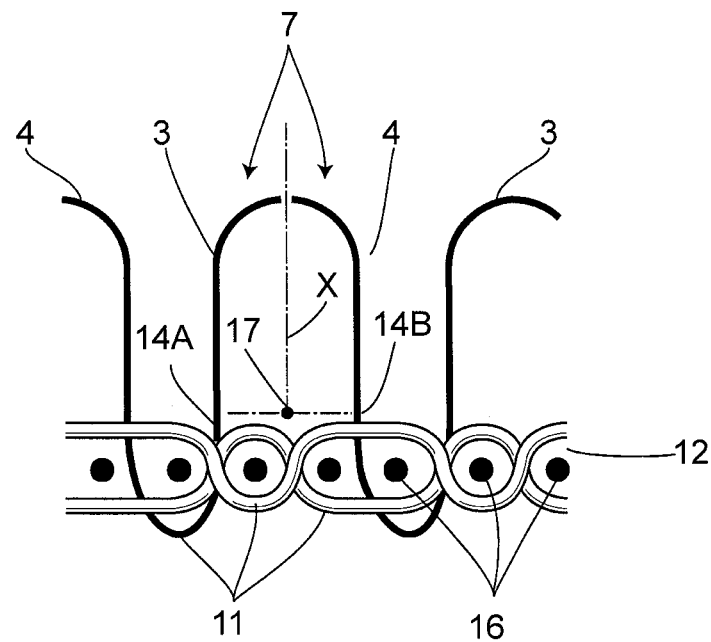
FIG. 6 is a cross-sectional view of a pile fabric having the thread members formed according to the first embodiment of the invention.

FIG. 6 shows an example of the shape of each of the first and second thread members 3, 4 that have been subjected to a cutting treatment at a top-vicinity region 6 of the loop of each thread member of the pile fabric. A tip end portion 7 as a free end of each of the first and second thread members 3, 4 is formed into a shape partially maintaining an arc shape of the loop. The first and second thread members 3, 4 are formed into shapes that are substantially line-symmetrical with each other with respect to a straight line X vertically rising from a center point 17 between the first protruding portion 14A and the second protruding portion 14B. Since a cut is made on the thread member 2, the first and second protruding portions 14A, 14B may fray. For this reason, the foundation main body 12 may also be provided with a retaining mechanism (not shown) established by, for example, adhesion or welding, for the purpose of preventing fraying.

In FIG. 6, although the thread member groups 5 each made of a bundle of the multiple thread members 2, are arranged in rows along the moving direction Z, the positions of these thread member groups 5 may be modified in various ways. For example, as shown in FIG. 7, thread member groups 5B on the second row may be transversely displaced with respect to thread member groups 5A on the first row so that tongue plaque between neighboring thread member groups 5A, 5A on the first row can be scraped off by the thread member groups 5B on the second row.

As a result of using the sheet 1 having the first and second thread members 3, 4, the first and second thread members 3, 4, as described above, are capable of move along the lingual papillae 301 as shown in FIG. 3A to FIG. 3C, and scraping therethrough in a manner such that the grime adhering to the circumferences of the lingual papillae 301 will be scraped off. Thus, the sheet having the first and second thread members 3, 4 can cleanly remove tongue plaque without damaging the lingual papillae 301.

Manufacturing Method

As mentioned above, there are known products where thread members as implanted hair are each formed into the shape of a hook or a half loop. However, there has never been known a specific sheet manufacturing method for forming the first and second thread members 3, 4 on, for example, a sheet employing a loop pile finer than implanted hair. Further, there has never been known a method for turning the tip end portion i.e. free end of each of the first and second thread members 3, 4 into the shape partially maintaining the arc shape of the loop.

Described hereunder is a method for manufacturing the sheet 1 having the aforementioned structure.

In the present embodiment, the thread members 2 are at first heated at a given temperature for a given period of time. The heating temperature is a temperature below the melting point of the thread members 2. For example, when employing nylon (registered trademark) as the thread members 2, the heating temperature may be 50 to 230° C., and the heating time may be several seconds to 60 min. When the heating temperature is extremely low, there may not be achieved the effect of turning the tip end portion 7 i.e. free end of each of the first and second thread members 3, 4 into the shape partially maintaining the arc shape of the loop. When the heating temperature is extremely high, the material of the thread members 2 will soften or melt. In view of mass production, it is preferred that the heating temperature be about 150 to 200° C., and that the heating time be about 3 to 5 min. The heating time may be shorter when the heating temperature is higher, whereas the heating time needs to be longer when the heating temperature is lower.

Figure 8:
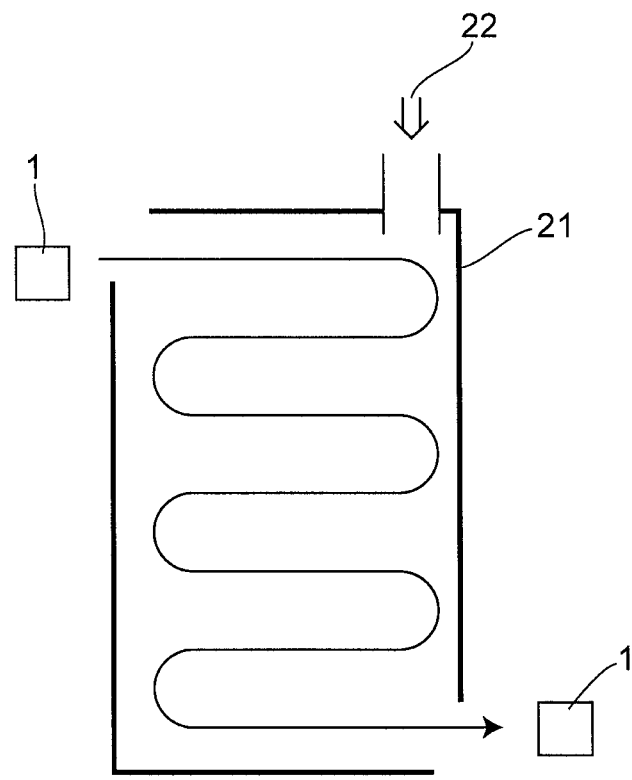
FIG. 8 is a schematic diagram showing an example of a heating device capable of being used in the embodiments of the invention.

There are no particular restrictions on a heating method. For example, there may be used a continuous heating device for heating the sheet 1 in a way such that the sheet 1 is moved, over a given period of time, inside a heating chamber 21 whose temperature has been raised by a hot air 22 or the like (FIG. 8). There may also be used a batch-type heating device (not shown) for heating the sheet 1 with the sheet 1 itself being fixed inside a housing such as a chamber.

Figures 9A, 9B:
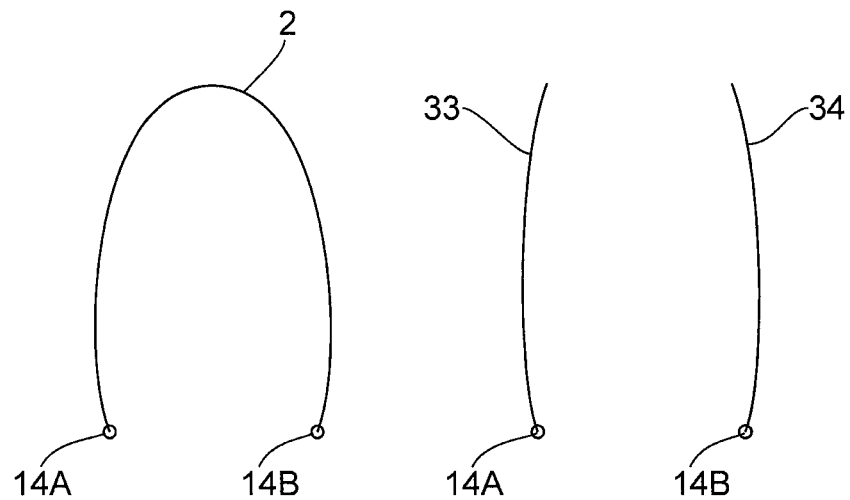
Figures 10A, 10B:
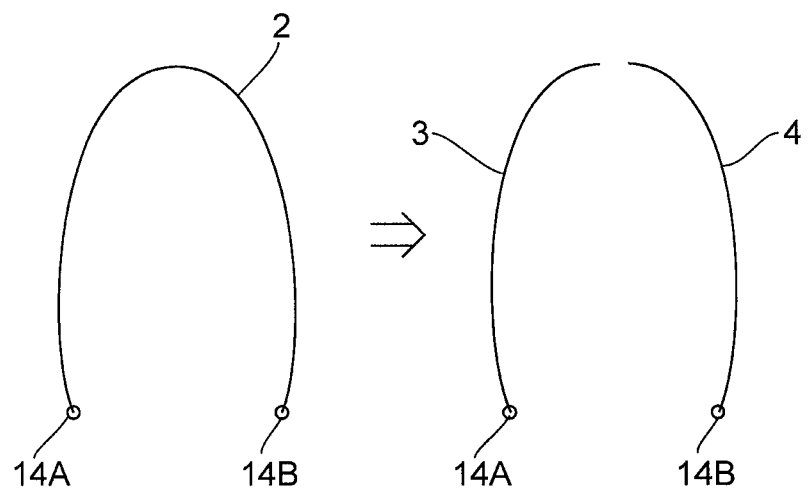
Figure 11:
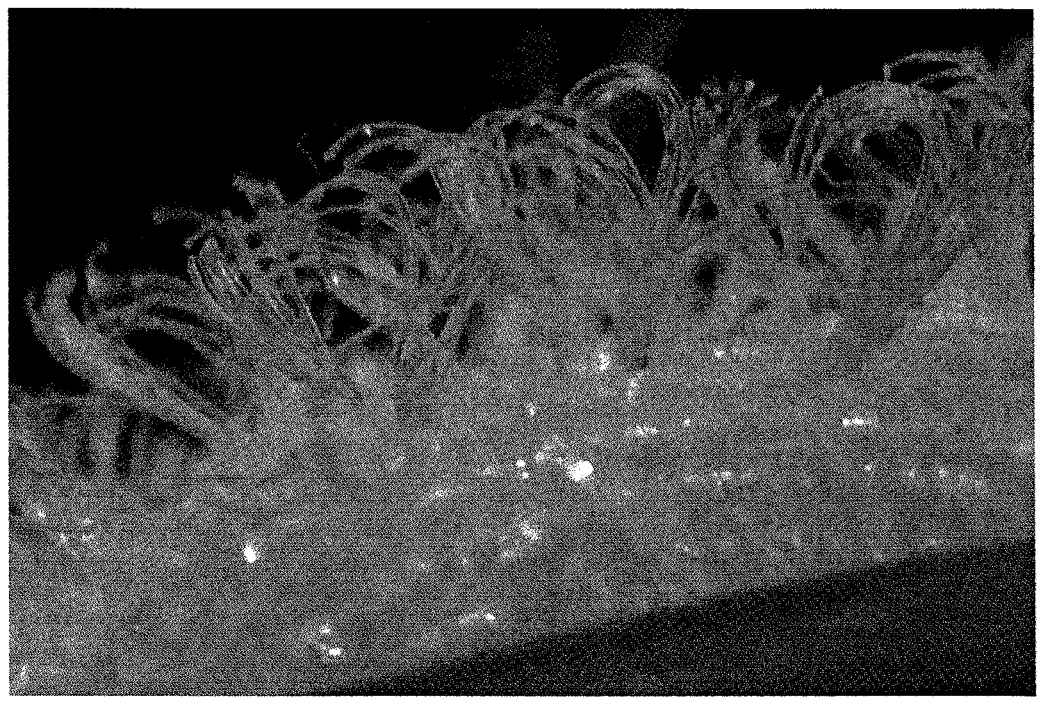
FIG. 11 is a photograph showing a state where the top-vicinity region of the loop of the heat-treated thread member has been cut.

If cutting the thread members 2 without performing such heating treatment, two thread members 33, 34 will become linear as shown in FIGS. 9A and 9B. In contrast, if cutting the thread members 2 after performing an appropriate heating treatment, the two first and second thread members can partially maintain their shapes that are exhibited before cutting, as shown in FIGS. 10A and 10B, so that these thread members can each be formed into a shape with an arc portion sufficient enough to scrape off tongue plaque. FIG. 11 is a photograph showing a state where a top-vicinity region of the loop of each thread member 2 has been cut after performing the heating treatment.

Therefore, in this embodiment, after performing the heating treatment on the thread members 2, the first and second thread members 3, 4 will be formed by using a cutting device to cut a part of the top-vicinity region 6 of the loop of each thread member. In this way, as shown in FIG. 12, the tip end portion 7 as the free end of each of the first and second thread members 3, 4 will be formed into the shape partially maintaining the arc shape of the loop. The tip end portions 7 of the multiple first and second thread members 3, 4 that have been cut as a bundle will then split from one another. There are no particular restrictions on the cutting device, as long as it is capable of cutting the thread members. For example, there may be used a cutlery having a blade in its cutting portion that will come into contact with the thread members 2. Also, the cutting treatment may be performed while performing the heating treatment. Here, if the cutting treatment is performed after the temperature of the thread members has decreased by, for example, natural cooling following the heating treatment, it will then be easy to cut the thread members in a manner that allows the tip end portion 7 as the free end of each of the first and second thread members 3, 4 to partially maintain the arc shape of the loop.

The aforementioned heating treatment is performed to fix the dimensions of the thread members 2 by heat so as to maintain their shapes and achieve a substantively perfect dimensional stability. As a result of releasing the internal strain by allowing time for sufficient internal relaxation in a given temperature range, irreversible shrinkage exhibiting different rates of shrinkage when heated and cooled can be prevented so that the shapes of the thread members 2 will be stabilized at temperatures not higher than the maximum temperature in the given temperature range. This is because irreversible shrinkage occurs due to a residual strain that is to be released at the given temperature. In this way, a substantively perfect dimensional stability can be achieved, and shape fixity as an effect can thus be achieved as well. Although the thread members 2 may be rapidly heated and/or cooled, it is preferred that they be gradually heated and/or cooled in order to sufficiently achieve the above effects.

The top-vicinity region 6 is such a region that a cutting site is extended by a given width in consideration of a case where the thread member is cut at a site slightly deviated from the site of a top point 18 of the loop due to the fact that the shapes of the loops of the thread members 2 may be slightly different from one another, and that some of the thread members may be slanted.

FIGS. 13A to 13C show how the top-vicinity region 6 of the loop of each thread member 2 is cut by a knife 41 as a cutting device having a blade 42 as a cutting portion. In FIG. 13A, the thread member 2 is moved in a moving direction D toward the knife 41 that is fixed in a manner such that its blade surface now faces upward against the top-vicinity region 6. A tip end 43 of the knife 41 is formed into a tapered shape (sharpened in the drawing) so that the knife 41 can easily enter the loop of the thread member 2. In FIG. 13B, since the blade 42 of the knife 41 has an inclined portion 44, the top-vicinity region 6 of the loop of the thread member 2 can come into contact with the blade 42 of the knife. In FIG. 13C, by further moving the thread member 2 in the moving direction D, the top-vicinity region 6 of the loop of the thread member 2 will be cut by the blade 42 of the knife 41 as a result of passing therebeyond.

As a method for cutting the top-vicinity regions 6 of the loops of multiple thread members 2, there may be employed a method shown in FIG. 14 where the top-vicinity regions 6 of the loops are cut by allowing the multiple thread members 2 to pass beyond multiple cutting devices 41 that are arranged with the surfaces of their blades as cutting portions 42 facing upward. The blade 42 has its surface positioned substantially perpendicular to the flat surface of the outer surface of the sheet 1 i.e. about 90° with respect to such flat surface.

The cutting method shown in FIG. 14 employs multiple cutting device groups 41A, 41B and 41C each composed of multiple knives 41 as cutting devices that are arranged in a row. A distance L1 between the neighboring cutting devices 41 is larger than a distance L2 between the neighboring thread members 2 (i.e. a distance between a midpoint 17A of a thread member 2A and a midpoint 17B of a thread member 2B). The multiple cutting devices 41 in the second cutting device group 41B are provided in locations that are deviated away from the multiple cutting devices 41 in the first cutting device group 41A in the moving direction D. The multiple cutting devices 41 in the third cutting device group 41C are provided in locations that are deviated away from the multiple cutting devices 41 in the second cutting device group 41B in the moving direction D. The scale of such deviation is determined by the distance between neighboring thread members. In the case of FIG. 14, the thread member 2A is cut by the first cutting device group 41A, the thread member 2B is cut by the second cutting device group 41B, and the thread member 2C is cut by the third cutting device group 41C. In this way, as a result of passing beyond the multiple cutting device groups 41A, 41B and 41C, the loops of all the thread members 2A, 2B and 2C can be cut at given sites. However, there are no particular restrictions on the number of the cutting device groups. When the distance between the neighboring thread members 2 is large, the distance between such neighboring thread members 2 can be made equal to the distance between the neighboring cutting devices 41 so that the loops of all the thread members can be cut with one cutting device group.

When the distance between the neighboring cutting devices 41 is larger than the distance between the neighboring thread members 2, the sheet 1 may at first simply pass beyond one cutting device group, followed by shifting the locations of the cutting devices 41 by a given magnitude so as to allow the sheet 1 to again pass beyond these cutting devices 41. The distance between the neighboring thread members 2 and the distance between the neighboring cutting devices 41 determine the magnitude by which the locations of the cutting devices 41 are to be shifted and the number of times for passing the sheet 1.

Also, instead of moving the sheet 1, the cutting devices 41 may be moved with the sheet 1 being fixed. Further, at that time, the cutting devices may be rotated as well.

Figure 15:
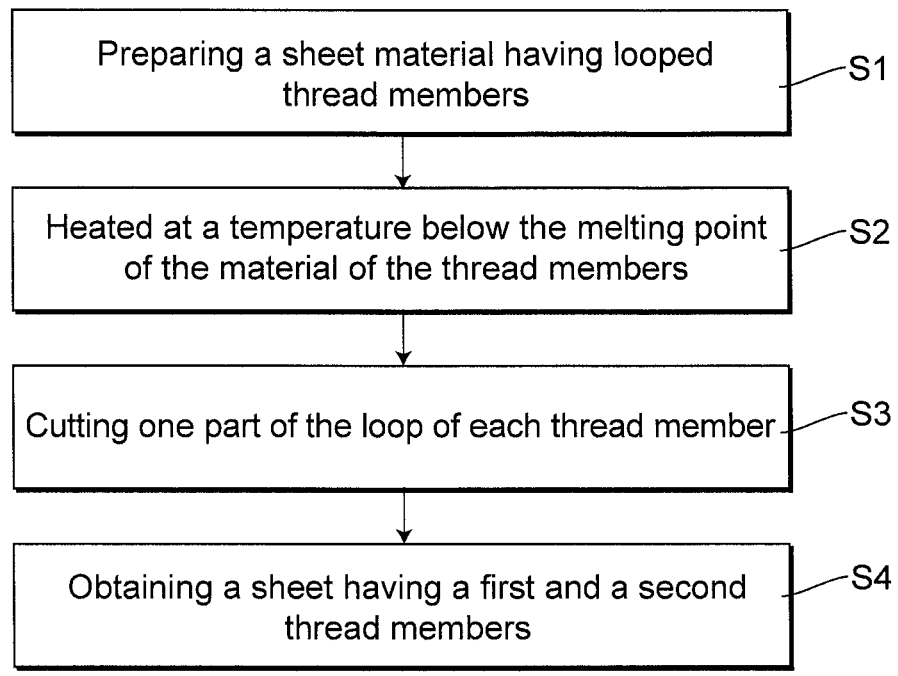
FIG. 15 is a flowchart of a method for manufacturing the sheet of the invention.

A simple summary of the manufacturing method of the present embodiment is shown in the flowchart of FIG. 15. In the beginning, there is prepared a sheet material having the looped thread members 2 (S1). Next, the thread members 2 are heated at a temperature lower than the melting point of the material of the thread members 2 (S2). After the heating treatment, one section (e.g. top-vicinity region 6) of the loop of each thread member 2 is cut (S3). In this way, there is obtained the sheet 1 having the first and second thread members 3, 4 (S4).

As described above, according to the method for manufacturing the sheet for tongue plaque cleaner of the present embodiment, the tip end portion 7 as the free end of each of the first and second thread members 3, 4 can be formed into the shape partially maintaining the arc shape of the loop. Thus, a sheet capable of efficiently removing tongue plaque without damaging the tongue can be manufactured through simple and low-cost steps.

Second Embodiment

Structure of Sheet

The structure of the sheet 1 prior to the cutting of the loops of the thread members 2 is similar to that of the first embodiment.

Figure 16:
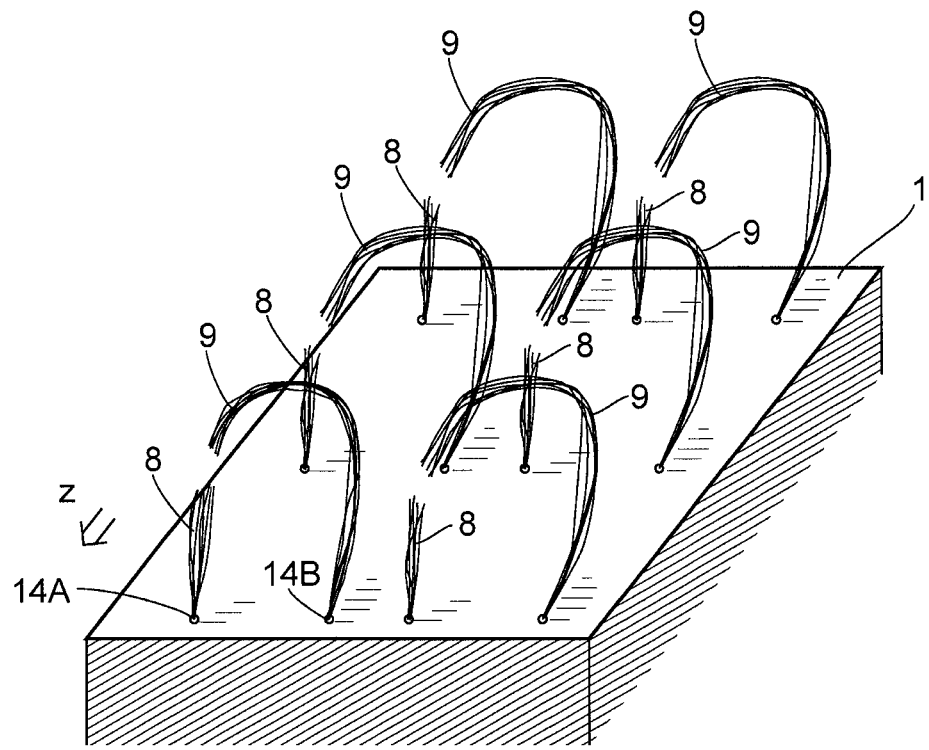
FIG. 16 is a perspective view showing a sheet having thread members formed according to a second embodiment of the invention.
Figure 17:
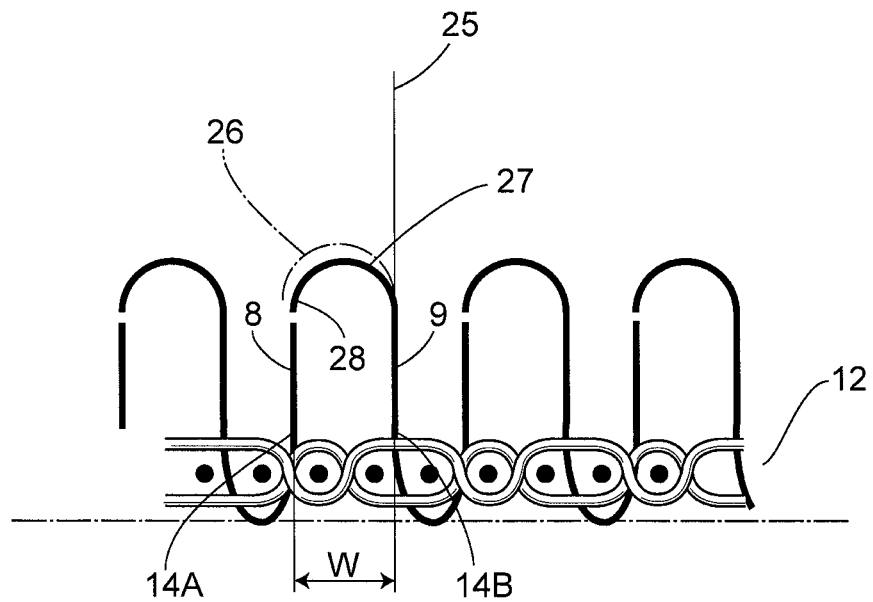
FIG. 17 is a cross-sectional view of a pile fabric having the thread members formed according to the second embodiment of the invention.
Figure 18A:
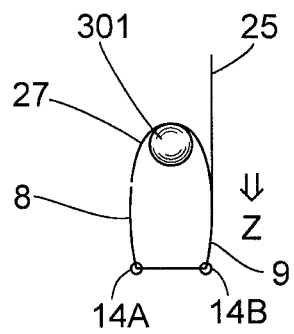
Figure 18B:
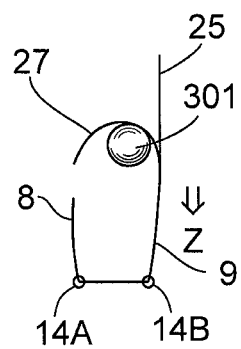
Figure 18C:
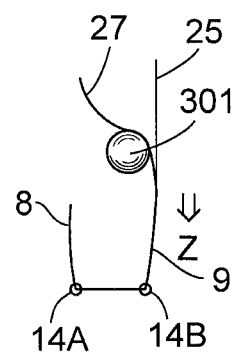
Figure 18D:
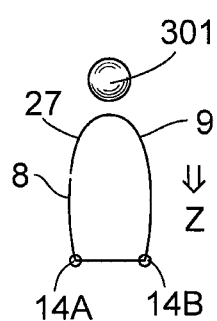

As a result of cutting any one of the side parts of the loop of each thread member 2, one part of the thread member will be turned into a reversed J shape, whereas the other part of the thread member will be turned into a substantially linear shape. In FIG. 16, the thread member 2 is cut by making a cut in one section on the side of the first protruding portion 14A, thus forming a substantially linear first thread member 8 and a reversed J-shaped second thread member 9. FIG. 17 shows an example of the shapes of the first and second thread members 8, 9 that are exhibited after the pile fabric has been subjected to the cutting treatment. The second thread member 9 has a bridge portion 27 as an overhanging portion formed in a manner such that a second longitudinal direction 26 that intersects with a first longitudinal direction 25 is now in a transverse direction. A tip end portion 28 of the bridge portion 27 is a free end. A substantially central part of the bridge portion 27 is formed into the shape of an arc protruding upward; and the tip end of the bridge portion 27 is folded back toward the foundation main body 12. Thus, the second thread member 9 is formed into the reversed J shape. It is preferred that a width direction W between the first protruding portion 14A and the second protruding portion 14B be formed orthogonal to the moving direction Z. Here, the thread member 2 may also be cut by making a cut in one section on the side of the second protruding portion 14B.

Since a cut is made on the thread member 2, the first and second protruding portions 14A, 14B may fray. For this reason, the foundation main body 12 may also be provided with a retaining mechanism (not shown) established by, for example, adhesion or welding, for the purpose of preventing fraying.

If employing the sheet 1 having the reversed J-shaped second thread members 9, since the tip end portion 28 of the bridge portion 27 is a free end, the bridge portion 27, when hooked on the lingual papillae 301, can deform along the first longitudinal direction 25 and then scrape through the lingual papillae 301, as shown in FIGS. 18A to 18D. Thus, the lingual papillae 301 can be prevented from being damaged.

Manufacturing Method

Described hereunder is a method for manufacturing the sheet 1 having the aforementioned structure.

As is the case with the first embodiment, the looped thread members 2 are also at first heated at a given temperature for a given period of time in the present embodiment. The conditions and method for the heating treatment are similar to those in the first embodiment. This embodiment differs from the first embodiment in the method for cutting the thread members 2.

Figure 19A:
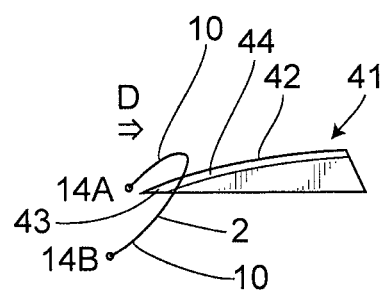
Figure 19B:
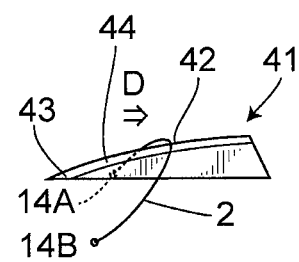
Figure 19C:
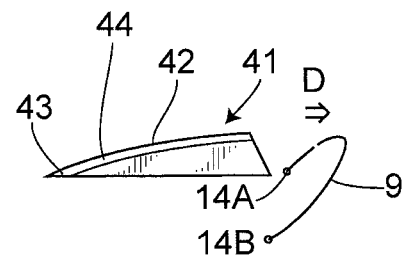

FIGS. 19A to 19C show how any one of side parts 10 of the loop of the thread member is cut by a knife as a cutting device 41 having a blade in its cutting portion 42. In FIG. 19A, the thread member 2 is moved in the moving direction D toward the knife that is fixed with the surface of the blade 42 transversely facing the direction of the side part 10. A tip end 43 of the knife 41 is formed into a tapered shape (sharpened in the drawing) so that the knife 41 can easily enter the loop of the thread member 2. In FIG. 19B, since the blade 42 of the knife 41 has the inclined portion 44, any one of the side parts 10 of the loop of the thread member 2 can come into contact with the blade 42 of the knife 41. In FIG. 19C, by further moving the thread member 2 in the moving direction D, any one of the side parts 10 of the loop of the thread member 2 will be cut by the blade 42 of the knife 41 as a result of passing therebeyond.

As a method for cutting any one of the side parts 10 of the loop of each of the multiple thread members 2, there may be employed, for example, a method where any one of the side parts 10 of the loop is cut by allowing each of the multiple thread members 2 to pass beyond multiple cutting devices 41 that are arranged with the surfaces of their blades as cutting portions 42 being arranged transversely. In the cutting method shown in FIG. 14, the surface of the blade 42 is substantially parallel to the flat surface of the outer surface of the sheet 1 i.e. about 0° with respect to such flat surface. The positions of the side parts 10 to be cut can be adjusted by either chaining the angle of the surface of the blade 42 within 0 to 90°, or changing the height of the cutting device 41 from the sheet 1. The only difference between the manufacturing method of this embodiment and that of the first embodiment is that the method of this embodiment employs a different orientation of the blade 42 of the cutting device 41; whereas similar methods may be used as for the rest part of the manufacturing process.

As is the case with the first embodiment, the manufacturing method of this embodiment also includes the steps shown in the flowchart of FIG. 15.

As described above, according to the method for manufacturing the sheet for tongue plaque cleaner of the present embodiment, the first thread member 8 can be formed into the substantially linear shape, and the second thread member 9 can be formed into the reversed J shape. Thus, a sheet capable of efficiently removing tongue plaque without damaging the tongue can be manufactured through simple and low-cost steps.

Evaluation

It has already been confirmed that the tongue plaque removal performance of the tongue plaque cleaner using the sheet for tongue plaque cleaner 1 that is manufactured by the manufacturing methods of the embodiments is the same as conventional tongue plaque cleaners having uncut thread members. A problem with a conventional tongue plaque cleaner having uncut thread members is that as a result of repeatedly using the cleaner to remove tongue plaque and then washing the sheet 1, grime will remain on the sheet 1 such that the sheet 1 will be stained in a relatively short period of time, which makes the cleaner unusable in such a short period of time as well. It was confirmed that the tongue plaque cleaner using the sheet 1 manufactured by the manufacturing methods of the embodiments exhibited not only an unimpaired removal performance; but also a property that grime can now easily come off so that the washed sheet 1 will only be stained in an insignificant manner, due to the fact that the thread members are cut. Further, it is also known that the number of the bacteria remaining on the washed sheet 1 is smaller than that of a sheet having uncut thread members. Furthermore, since the shapes of the washed first thread members 3, 8 and second thread members 4, 9 do not change easily, the tongue plaque cleaner of the invention can be continuously used for a long period of time.

However, the present invention is not limited to the aforementioned embodiments, and various modifications can be made within the scope of the gist of the present invention. For example, the sheet 1 manufactured by the manufacturing method of the invention may not only be used for the purpose of removing tongue plaque; but also be used for the purpose of cleaning parts in the entire oral cavity other teeth, such as the upper jaw, rear side of cheek, gum, and an area between teeth and lips; or even be used for the purpose of whitening teeth. Further, the first and second embodiments may be combined with each other. That is, the thread members 3, 4 each formed by cutting the top-vicinity region 6 of the loop; and the thread members 8, 9 each formed by cutting any one of the side parts 10 of the loop may coexist. In such case, with regard to the cutting method shown in FIG. 14, there may be used in combination the cutting devices 41 with the cutting portions 42 facing upward; and the cutting devices 41 with the cutting portions 42 facing a transverse direction. Particularly, the cutting devices 41 may not only face upward and the transverse direction; by changing the angles of the cutting devices 41 so as to allow them to face various directions, there can be obtained a sheet 1 having thread members with different cutting sites.

What is claimed is:

1. A method for manufacturing a sheet for use in a tongue plaque cleaner for scraping off tongue plaque, comprising:
   a step of heating a sheet material having multiple looped thread members protruding from one surface of the sheet material at a temperature below the melting point of the thread members; and
   a step of forming first and second thread members by cutting loops of the thread members that were heated, wherein
   the loops of the threaded members are cut by multiple cutting devices as a result of horizontally moving the sheet material to pass beyond the multiple cutting devices, or by moving the multiple cutting devices in a direction parallel to the one surface of the sheet material while the sheet material is fixed,
   all of the multiple cutting devices are fixedly arranged in a row in a direction perpendicular to a moving direction of the sheet material or multiple cutting devices,
   the sheet material is heated in such a manner that the first and the second thread members maintain their shapes that were exhibited before cutting, and
   a distance between the multiple cutting devices that neighbor each other in the direction perpendicular to the moving direction is larger than a distance between the thread members that neighbor each other in the direction perpendicular to the moving direction.

2. The method for manufacturing the sheet for use in the tongue plaque cleaner according to claim 1, wherein a top-vicinity region of the loop of each of the looped thread members is cut in a manner such that a tip end portion as a free end of each of the first and second thread members can be formed into a shape partially maintaining an arc shape of the loop.

3. The method for manufacturing the sheet for use in the tongue plaque cleaner according to claim 2, wherein the top-vicinity regions of the loops of the multiple looped thread members are cut by the multiple cutting devices arranged with cutting portions thereof facing the top-vicinity regions of the loops.

4. The method for manufacturing the sheet for use in the tongue plaque cleaner according to claim 1, wherein top-vicinity regions of the loops of the multiple looped thread members are cut by the multiple cutting devices arranged with cutting portions thereof facing the top-vicinity regions of the loops.

5. The method for manufacturing the sheet for use in the tongue plaque cleaner according to claim 1, wherein one of side parts of the loop of each of the looped thread members is cut to turn the first thread member into a substantially linear shape, and the second thread member into a reversed J shape.

6. The method for manufacturing the sheet for use in the tongue plaque cleaner according to claim 5, wherein any one of the side parts of the loop of each of the multiple looped thread members is cut by the multiple cutting devices arranged with cutting portions thereof each facing one of the side parts of the loop.

7. The method for manufacturing the sheet for use in the tongue plaque cleaner according to claim 1, wherein any one of side parts of the loop of each of the multiple looped thread members is cut by the multiple cutting devices arranged with cutting portions thereof each facing one of the side parts of the loop.

8. The method for manufacturing the sheet for use in the tongue plaque cleaner according to claim 1, wherein a site at which the loop of each of the multiple looped thread members is cut differs from the thread member to the thread member, and the multiple looped thread members are cut by the multiple cutting devices arranged with cutting portions thereof facing different directions ranging from a top-vicinity region of the loop to side parts thereof, thereby forming multiple thread members having different cutting sites.

9. The method for manufacturing the sheet for use in the tongue plaque cleaner according to claim 1, wherein the thread members are made of a thermoplastic resin.

10. The method for manufacturing the sheet for use in the tongue plaque cleaner according to claim 1, wherein a first cutting device group, a second cutting device group and a third cutting device group are provided,
    each of said cutting device groups comprises the multiple cutting devices, and
    each of the loops is respectively cut by each of the multiple cutting devices.

11. The method for manufacturing the sheet for use in the tongue plaque cleaner according to claim 10, wherein the cutting devices in the second cutting device group are provided in locations that are deviated away from the cutting devices in the first cutting device group in a direction of moving the sheet material or the multiple cutting devices.

12. The method for manufacturing the sheet for use in the tongue plaque cleaner according to claim 10, wherein the cutting devices in the third cutting device group are provided in locations that are deviated away from the cutting devices in the second cutting device group in a direction of moving the sheet material or the multiple cutting devices.

13. The method for manufacturing the sheet for use in the tongue plaque cleaner according to claim 1, wherein the sheet material is heated at 150 to 200° C. for 3 to 5 minutes.

14. The method for manufacturing the sheet for use in the tongue plaque cleaner according to claim 1, wherein each of the first and second thread members after cutting contains an arc shape portion sufficient enough to scrape off tongue plaque.

15. The method for manufacturing the sheet for use in the tongue plaque cleaner according to claim 1, wherein each of the multiple cutting devices has a blade surface and is fixed in a manner such that the blade surface faces upward against a top-vicinity region of each of the loops.

16. The method for manufacturing the sheet for use in the tongue plaque cleaner according to claim 1, wherein the multiple cutting devices have blades that face in various directions so that a plurality of thread members having different cutting sites are formed.

17. The method for manufacturing the sheet for use in the tongue plaque cleaner according to claim 16, wherein an angle of each of the blades is in a range of 0 to 90 degrees with respect to the one surface of the sheet material.

* * * * *